US00PP19581P2

(12) United States Plant Patent
Neubauer

(10) Patent No.: US PP19,581 P2
(45) Date of Patent: Dec. 16, 2008

(54) ***LIRIODENDRON* PLANT NAMED 'LITTLE VOLUNTEER'**

(50) Latin Name: *Liriodendron*
Varietal Denomination: Little Volunteer

(76) Inventor: Alexander Neubauer, 214 Tanager Hill La., Belvidere, TN (US) 37306-2129

( * ) Notice: Subject to any disclaimer, the term of this patent is extended or adjusted under 35 U.S.C. 154(b) by 0 days.

(21) Appl. No.: 12/008,123

(22) Filed: Jan. 8, 2008

Related U.S. Application Data

(60) Provisional application No. 60/880,852, filed on Jan. 16, 2007.

(51) Int. Cl.
*A01H 5/00* (2006.01)

(52) U.S. Cl. ..... Plt./216
(58) Field of Classification Search ..... Plt./216
See application file for complete search history.

*Primary Examiner*—Annette H Para
*Assistant Examiner*—S. B. McCormick

(57) ABSTRACT

A new cultivar of *Liriodendron* plant named 'Little Volunteer' that is characterized by very dwarf habit, having overall dimensions which are approximately one-third of the dimensions of the species, and thereby setting 'Little Volunteer' apart from all other varieties of *Liriodendron* known to the inventor.

3 Drawing Sheets

Genus: *Liriodendron*. Species: *tulipfera*.
Denomination: 'Little Volunteer'.

BACKGROUND OF THE INVENTION

This application claims the benefit of priority under 35 U.S.C. 119(e) of U.S. Provisional Application No. 60/880,852 filed on Jan. 16, 2007, entitled *Liriodendron* Plant named 'Little Volunteer'.

The present invention relates to a new and distinct cultivar of *Liriodendron* commonly known as Tulip Tree or Tulip Poplar, which is grown as an ornamental tree for use in street plantings and in residential landscapes. The new cultivar is known botanically as *Lirodendron tulipfera* and will be referred to hereinafter by the cultivar name 'Little Volunteer'.

'Little Volunteer' was discovered and selected in Spring 2001 by the inventor at the inventor's nursery in Belvidere, Tenn. as a single naturally occurring plant with novel dwarf habit which the inventor found growing within the inventor's seed-grown crop of *Liriodendron*. The inventor is unable to identify either the male or the female parent.

'Little Volunteer' exhibits dwarf habit compared to the typical species. Mature trees of 'Little Volunteer' are approximately ⅓ the size of a typical *Liriodendron tulipfera* specimen which reaches a mature size of 30 feet in height and 20 feet in width. The closest known cultivar known to the inventor is the cultivar *Liriodendron* 'Ardis' (unpatented). The leaf shape of 'Little Volunteer' is more typical of the species and maintains a central leader better than 'Ardis'.

'Little Volunteer' was first asexually propagated by the inventor in Belvidere, Tenn. in Fall 2002. Asexual propagation was accomplished by grafting 'Little Volunteer' onto seedling understock. Since that time, under careful observation, the distinguishing characteristics of 'Little Volunteer' have been determined stable and uniform, and are reproduced true to type in successive generations of asexual propagation.

SUMMARY OF THE INVENTION

The following traits have been repeatedly observed and represent the characteristics of the new *Liriodendron* cultivar 'Little Volunteer'. These traits in combination distinguish 'Little Volunteer' from all other varieties of *Liriodendron* known to the inventor. 'Little Volunteer' has not been tested under all possible conditions and phenotypic differences may be observed with variations in environmental, climatic and cultural conditions, without however any change in genotype.

1. 'Little Volunteer' is a very dwarf form of *Liriodendron*.
2. The plant shape of 'Little Volunteer' is rounded pyramidal.
3. After four years growth from a transplanted liner plant, 'Little Volunteer' achieves a height of 4 meters and a width of 2 meters, and an average trunk diameter of 60 mm.
4. The dimensions of the foliage of 'Little Volunteer' are approximately one-third of the dimensions of the species or known cultivars of *Liriodendron*.
5. 'Little Volunteer' grows well in moist well-drained soils in full sun to partial shade.
6. 'Little Volunteer' is hardy to USDA Zone 4.

BRIEF DESCRIPTION OF THE DRAWINGS

The accompanying color drawings illustrate the overall appearance of the new *Liriodendron* variety 'Little Volunteer' showing colors as true as it is reasonably possible to obtain in colored reproductions of this type. Colors in the drawings may differ from the color values cited in the detailed botanical description, which accurately describe the actual colors of the new variety 'Little Volunteer'.

The drawing labeled

The drawing labeled

The drawing labeled

Figure 1:
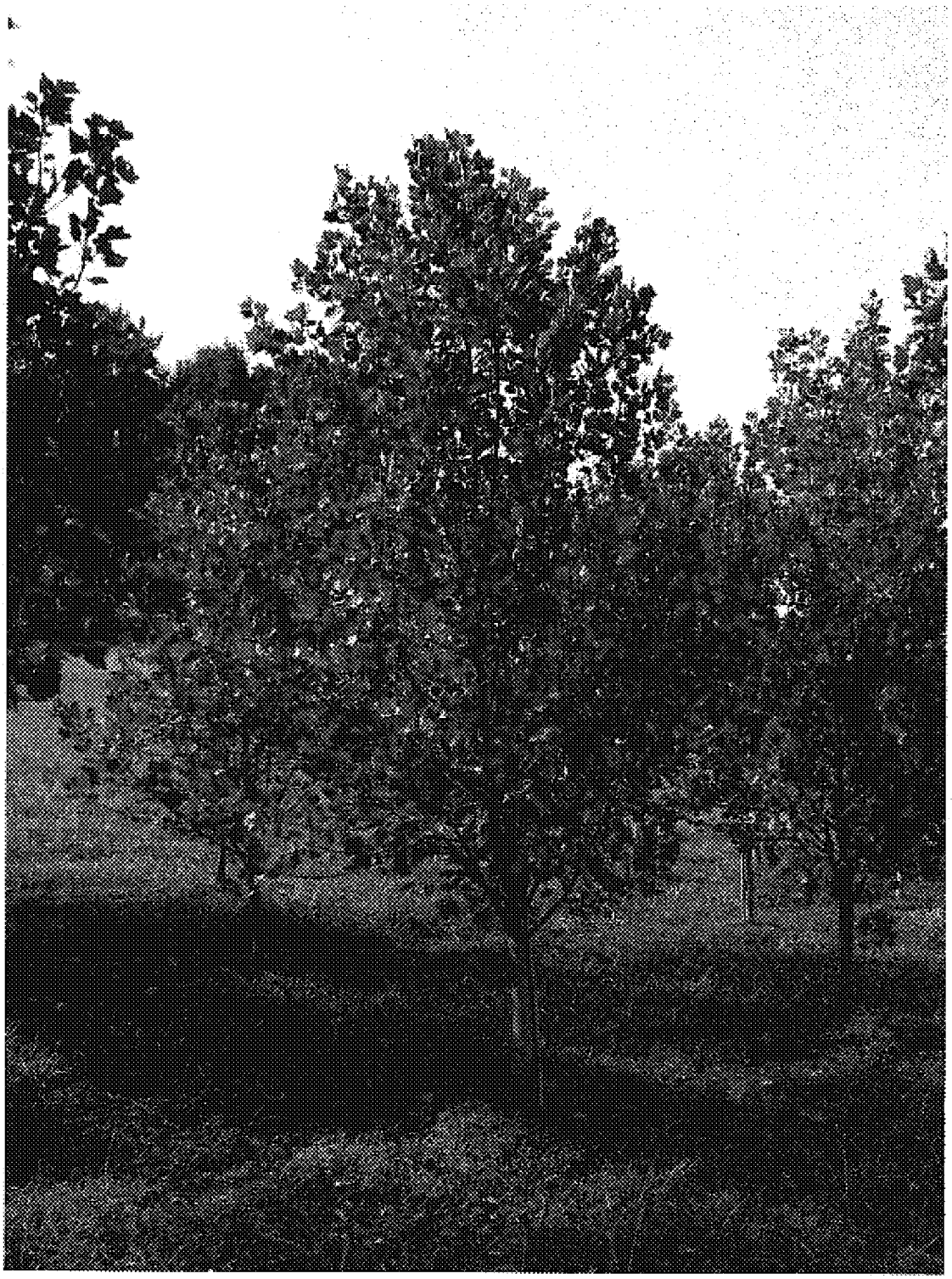
FIG. 1 shows a four year old plant of 'Little Volunteer' growing in the field in Belvidere, Tenn. The drawing illustrates the rounded pyramidal shape of 'Little Volunteer'. The plant depicted is approximately 4 meters in height and 2 meters in width.
Figure 2:
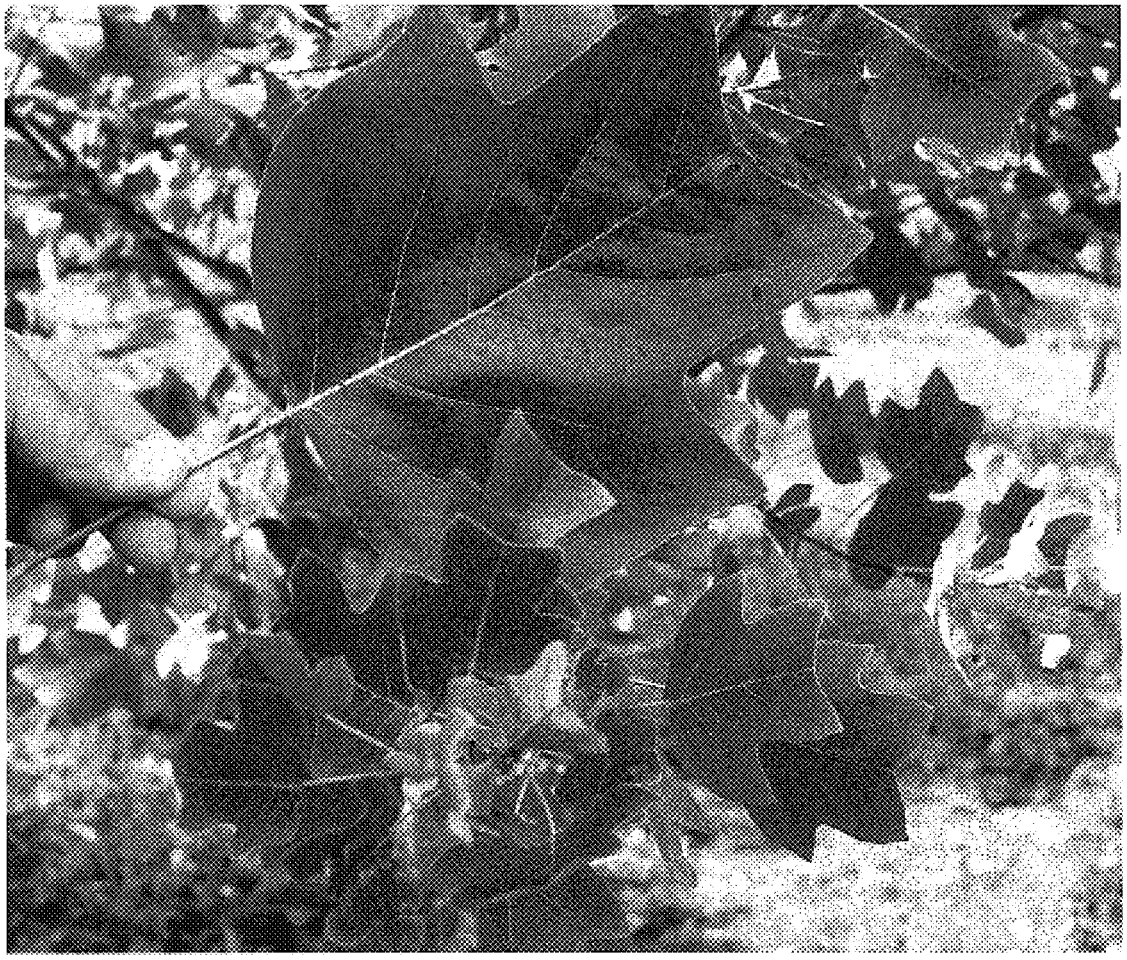
FIG. 2 illustrates the exceptionally small foliage of 'Little Volunteer'. All of the leaves shown in the drawing are leaves of 'Little Volunteer' except for the single leaf which is hand-held and which has been taken from a nearby plant of the species *Liriodendron,* of similar age.
Figure 3:
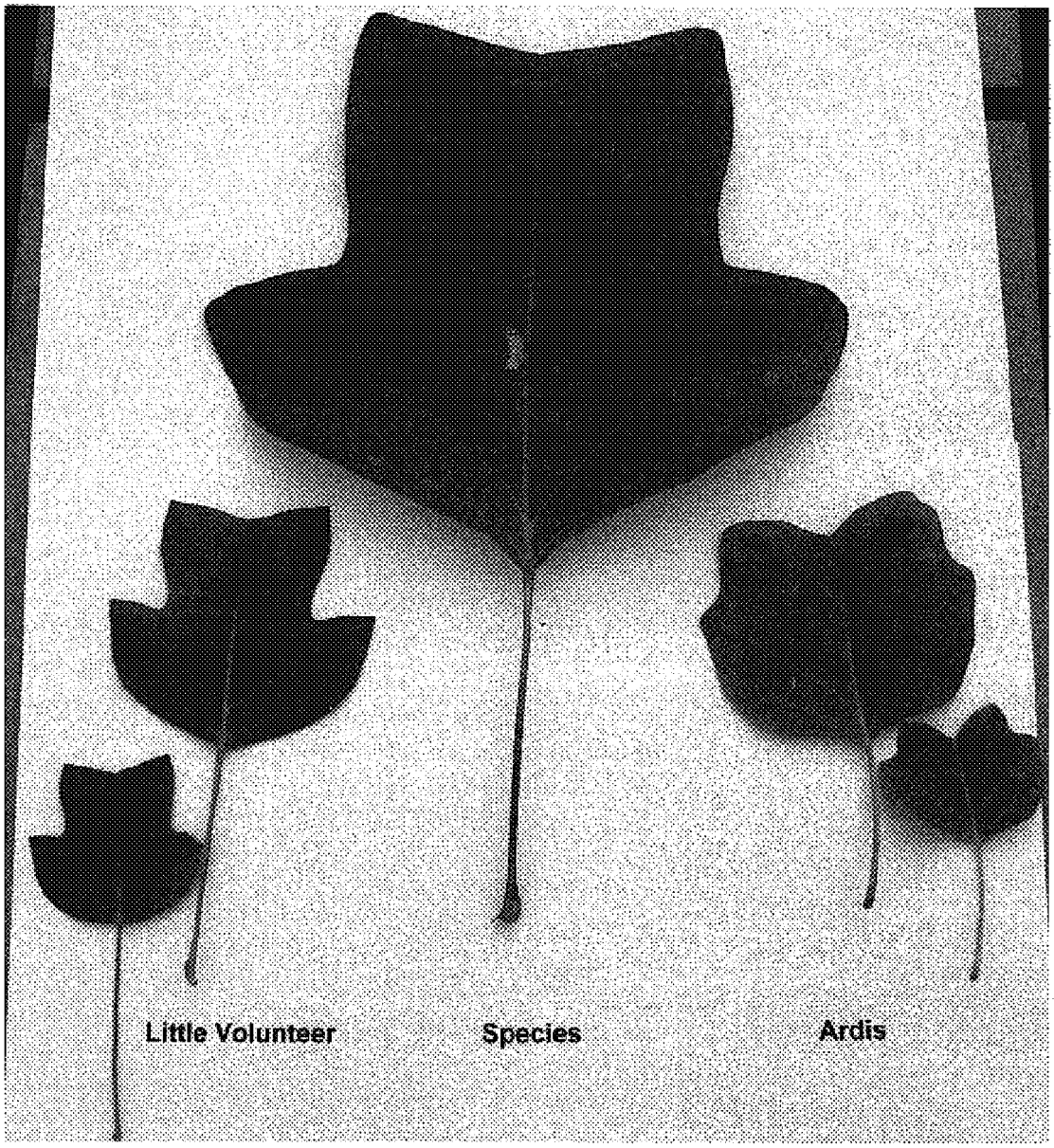
FIG. 3 shows a comparison of the leaves of 'Little Volunteer', a typical *Liriodendron tulipfera,* and 'Ardis'.

All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'Little Volunteer'. Data was collected from plants approximately 4 years old from initial budding grown in out of doors in Raleigh, N.C. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions are typical to other *Liriodendron.*

Botanical classification: *Liriodendron.*
Species: *tulipfera.*
Common name: Tulip tree.
Commercial classification: Deciduous tree.
Use: Landscape plant.
Parentage:
*Female parent plant.*—Unknown.
*Male parent plant.*—Unknown.
Plant description:
*Plant habit.*—Compact pyramidal.
*Plant dimensions* (*after first year*).—Approximately 1.3 m in height and 0.75 m in width.
*Plant dimensions* (*after four years from a transplanted liner plant*).—4 m in height and a width of 2 m, and an average trunk diameter of 60 mm.
*Estimated plant dimensions at maturity.*—9 m in height and 6 m in width.
*Plant hardiness.*—USDA Zone 4 to 9.
*Type.*—Deciduous tree.
*Propagation.*—Propagation is accomplished by budding or grafting.
*Cultural requirement.*—Moist well-drained soils in full sun to partial shade.
*Diseases and pests.*—No susceptibility or resistance of note.
*Branching habit.*—Ascending.
Trunk:
*Dimensions.*—2–2.5 m in height, 60 mm in diameter at 10 cm above ground level.
*Bark surface.*—Smooth, becoming furrowed with rough rounded ridges with age.
*Color.*—198C.
*Lenticels.*—None present.
Branches:
*Color.*—Current season, 200D; previous season, 197A.
*Branch surface.*—Smooth.
*Diameter.*—4 cm.
*Internode distance.*—Ranges from 5 mm to 15 mm.
*Lenticels.*—None present. Foliage:
*Type.*—Deciduous.
*Leaf buds.*—Terminal buds present in winter, 1.0–1.5 cm in length, 0.8–1.2 cm in width.
*Shape.*—Flattened, valvate.
*Color.*—177A.
*Leaves.*—Shape: Rounded to obovate. Arrangement: Alternate Division: Simple Margins: Entire. Dimensions: 4 cm to 6.5 cm in length and 5 cm to 7.75 cm in width. Apex: Truncate. Base: Cordate to truncate. Venation pattern: Palmate. Vein color (adaxial): 144C. Vein color (abaxial): 150D. Margin type: Entire. Leaf surface (adaxial and abaxial): Glabrous. Mature leaf color (adaxial): 139A. Mature leaf color (abaxial): 146C. Young leaf color (adaxial): 139A. Young leaf color (abaxial): 147C. Leaf attachment: Petiolate. Petiole dimensions: 5.5 cm to 6.25 cm in length and 2 mm in diameter. Petiole surface: Glabrous. Petiole color: 144B.
Inflorescence: None observed. No plants of 'Little Volunteer' have produced flowers at time of filing this application.

What is claimed is:

1. A new and distinct cultivar of *Liriodendron* plant named 'Little Volunteer' as described and illustrated herein.

* * * * *